United States Patent [19]

Prescher et al.

[11] 4,087,454
[45] May 2, 1978

[54] PROCESS FOR THE PREPARATION OF PERPROPIONIC ACID SOLUTIONS

[75] Inventors: Gunter Prescher, Hanau; Otto Weiberg, Neu-Isenburg; Helmut Waldmann, Leverkusen; Hermann Seifert, Cologne, all of Germany

[73] Assignees: Deutsche Gold- und Silber-Scheideanstalt Vormals Roessler, Frankfurt am Main; Bayer Aktiengesellschaft, Leverkusen, both of Germany

[21] Appl. No.: 678,821

[22] Filed: Apr. 28, 1976

[30] Foreign Application Priority Data

Apr. 30, 1975 Germany .............................. 2519299

[51] Int. Cl.² ........................................... C07C 179/10
[52] U.S. Cl. ................................................ 260/502 R
[58] Field of Search ........................ 260/502 R, 502 A

[56] References Cited

FOREIGN PATENT DOCUMENTS 735,489  5/1966  Canada .............................. 260/502 R
744,391  10/1966  Canada .............................. 260/502 R Primary Examiner—Bernard Helfin
Assistant Examiner—Werren B. Lone
Attorney, Agent, or Firm—Burgess, Dinklage & Sprung

[57] ABSTRACT

In the production of perpropionic acid by reaction of hydrogen peroxide and propionic acid in an aqueous medium and in the presence of an acid catalyst, e.g. sulfuric acid, to produce the peracid and water, the danger of explosion is reduced by employing a molar ratio of hydrogen peroxide to propionic acid of less than 1.4:1, a temperature of up to 60° C, and an initial hydrogen peroxide:water ratio of up to 1.2, and a catalyst concentration of 10–40% of weight.

6 Claims, No Drawings

PROCESS FOR THE PREPARATION OF PERPROPIONIC ACID SOLUTIONS

The following applications are related to the process hereof for production of propylene oxide as being directed to aspects of the process, some of which are disclosed herein.

| German Serial No. | U.S. Atty's. Docket No. | U.S. Serial No. |
|---|---|---|
| P 25 19 288.5 | Bayer 2883 | 678,819 |
| P 25 19 300.4 | Bayer 2884 | 678,820 |
| P 25 19 298.7-42 | Bayer 2886 | 678,822 |
| P 25 19 297.6 | Bayer 2887 | 678,823 |
| P 25 19 295.4 | Bayer 2888 | 678,824 |
| P 25 19 293.2-42 | Bayer 2889 | 678,825 |
| P 25 19 292.1-42 | Bayer 2890 | 678,826 |
| P 25 19 291.0-42 | Bayer 2891 | 678,827 |
| P 25 19 289.6 | Bayer 2892 | 678,828 |
| P 25 19 297.4 | Bayer 2893 | 678,829 |

All of the German applications were filed Apr. 30, 1975. Those applications are incorporated herein by reference.

BACKGROUND

The present invention relates to a process for the preparation of perpropionic acid from hydrogen peroxide and propionic acid.

The synthesis of perpropionic acid from hydrogen peroxide and propionic acid is known (Swern, Organic Peroxides I, Wiley 1970, page 369-372). The reaction of hydrogen peroxide with propionic acid takes place in the presence of an acid catalyst according to equation (1)

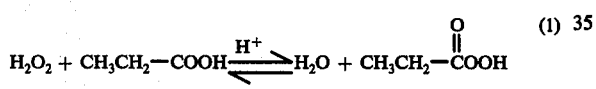

to give an equilibrium mixture which contains perpropionic acid, propionic acid, hydrogen peroxide, water and the acid catalyst. The concentration of perpropionic acid depends on the concentration of the feed materials and the molar feed ratio of hydrogen peroxide and propionic acid. In general, hydrogen peroxide is used in concentrations of 30 to 90% by weight, preferably 50 to 70% by weight. Propionic acid is preferably employed in the pure form or as an aqueous solution.

Suitable acid catalysts are the mineral acids, for example sulphuric acid, acid salts, such as, for example, sodium bisulphate, or cation exchangers based on sulphonated, partially crosslinked polystyrenes in the H+ ion form. The amount of these catalysts can vary within wide limits.

The mixtures formed according to the equation (1) can be used in a known manner for oxidation reactions.

The equilibrium mixtures formed according to equation (1) also arise as intermediates in processes for the preparation of anhydrous perpropionic acid solutions (DT-OS (German Published Specification No.) 2,262,970).

It is therefore extremely important to be able to prepare and handle the said reaction mixtures under explosion-proof conditions.

THE INVENTION

It is known that aqueous hydrogen peroxide, especially in a concentrated form, can form, with organic substances, mixtures which are capable of explosion and which present an explosion hazard. The explosibility of the lower percarboxlyic acid in bulk and in their solutions is also known. Surprisingly, however, it was shown that reaction mixtures such as are formed by the reaction of hydrogen peroxide with propionic acid in the presence of sulphuric acid according to equation (1) present an explosion hazard even when 50% strength by weight hydrogen peroxide, that is to say a ratio by weight of hydrogen peroxide : water = 1, and anhydrous propionic acid are used.

It has now been found, surprisingly, that perpropionic acid can be prepared by reaction of hydrogen peroxide with propionic acid in the presence of sulphuric acid under explosion-proof conditions when the reaction of hydrogen peroxide with propionic acid in the presence of sulphuric acid is carried out using a molar ratio of hydrogen peroxide : propionic acid employed of less than 1.4 : 1, the reaction temperature is restricted to a maximum of 60° C and the ratio of hydrogen peroxide (100% by weight) : water by weight before the start of the reaction with propionic acid is restricted to a maximum of 1.2:1 the sulphuric acid concentration in the reaction mixture being 10 to 40% by weight.

Contrary to all expectations it has been found, when the reaction mixtures, under conditions of partial, well defined enclosure in steel bombs, are exposed to heat and when the reaction mixtures are subjected to the detonation shock of a primer charge whilst enclosed in a steel tube (Explosivstoffe 9, 4 (1961) ), that reaction mixtures such as are formed according to equation (1) are explosion-proof when the molar ratio of hydrogen peroxide : propionic acid employed is restricted to less than 1.4:1, preferably 0.8-1.3:1, the reaction temperature is restricted to a maximum of 60° C and the ratio of hydrogen peroxide (100% by weight):water by weight before the start of the reaction with propionic acid is restricted to a maximum of 1.2, the sulphuric acid concentration in the reaction mixture being 10-40% by weight. An increase in the molar ratio of hydrogen peroxide:propionic acid employed for example from 1.3 to 1.5, at the same feed concentration of hydrogen peroxide, already results in a reaction mixture which at 60° C exhibits the properties of a high blasting explosive.

The reaction temperature in the preparation of the reaction mixtures is generally between 20° and 60° C, preferably 30-45° C and preferentially 35-40° C.

The present invention is illustrated by the tests which follow and the term explosion hazard, which is used there, is also explained.

EXAMPLE

There are various methods for assessing the explosion hazard of materials. For the present invention, the behaviour of the reaction mixtures when exposed to heat under conditions of partial, well-defined enclosure and the behaviour when subjected to the detonation shock of a primer charge were used to assess the explosion hazard of reaction mixtures which are formed by the reaction of hydrogen peroxide with propionic acid in the presence of sulphuric acid.

A method for determining the sensitivity of explosive materials towards exposure to heat, which leads to differentiated, comparable numerical values, is to heat the materials in a steel bomb which is closed off by a nozzle plate with a well-defined orifice. The steel bomb is fabricated from deep-drawing sheet metal and has an internal diameter of 24 mm, a length of 75 mm and a wall thickness of 0.5 mm. At its open end, the bomb is provided with a collar. The bomb is closed by a circular nozzle plate provided with a bore. Nozzle plates having the following diameters for the cylindrical outlet orifice for the gases produced by the decomposition are used: 1; 1.5; 2; 2.5; 3; 3.5; 4; 5; 6; 8; 10; 12; 14; 16 and 20 mm. The materials to be investigated are introduced into the steel bombs and, in order to prevent the initiation of a catalytic decomposition, the walls of the steel bomb can be provided with a coating of polyethylene or the like. The volume of the material sample is about 27 ml. The samples are exposed to heat by supplying heat in an amount of, on average, 2.4 kcals/sec from 4 Teclu-burners. With 3 tests, at least one explosion must take place, the bomb being split into 3 or more parts ("limiting diameter"). The limiting diameter determined in this way is to be regarded as a measure of the heat sensitivity of the material examined. The higher the limiting diameter, the higher is the heat sensitivity. Values of 2 – 2.5 mm are to be regarded as transition values into the dangerous range, values in excess of 2.5 mm indicating that the reaction is dangerously heat-sensitive.

The results of the investigations carried out on the reaction mixtures by the method described above are shown in the table which follows.

In order to obtain further data on the explosion hazard of the reaction mixtures, the behaviour of the reaction mixtures when subjected to the detonation shock of a primer charge, under conditions of enclosure, was investigated. For this purpose about 940 ml of the reaction mixtures were exposed, while enclosed in a 2 inch steel tube, to the detonation shock of a primer charge of 50 g of cyclonite with 5% of wax. In the present case, the conditions were further intensified by the temperature being raised to 60° C and the reaction mixtures being treated with oxygen gas by adding quartz pebbles coated with palladium. Seamless drawn 2 inch steel tubes havng a wall thickness of 5 mm and a length of 500 mm and with a welded-on base were used for the experiments. A cap was screwed to the open end and the auxiliary charge was fastened to the inside of the cap. The cap has a bore for the electric fuse with the detonator. This method gives a clear result with regard to the explosibility of a material and it indicates whether the explosion induced was propagated wholly, partly or not at all or whether the tube was disintegrated into splinters. The reaction mixtures tested were prepared from hydrogen peroxide of the indicated concentration using anhydrous propionic acid and concentrated sulphuric acid. The proportion of sulphuric acid was 30% by weight, relative to the mixture of aqueous hydrogen peroxide and propionic acid.

The results of the steel bomb tests and of the 2 inch steel tube tests are given in the table which follows:

| | Ratio by weight of hydrogen peroxide:water in the hydrogen peroxide charged | Molar ratio of hydrogen peroxide: propionic acid employed | Steel bomb limiting diameter (mm) | 2" steel tube with primer charge |
|---|---|---|---|---|
| 1) | 1.0 | 0.5 | 1.5 | |
| 2) | 1.0 | 0.8 | — | no explosion |
| 3) | 1.0 | 1.0 | 2 | no explosion |
| 4) | 1.0 | 1.2 | — | no explosion |
| 5) | 1.0 | 1.5 | 2.5 | complete explosion |
| 6) | 1.22 | 0.8 | 2 | |
| 7) | 1.22 | 1.0 | 2 | no explosion |
| 8) | 1.22 | 1.2 | 2.5 | no explosion |
| 9) | 1.22 | 1.3 | — | no explosion |
| 10) | 1.22 | 1.4 | — | complete explosion |
| 11) | 1.22 | 1.5 | 4 | |

As can be seen from the table, the range in which there is an explosion hazard is reached when the ratio by weight of hydrogen peroxide : water in the hydrogen peroxide charged is restricted to a maximum of 1.22 but the molar ratio of hydrogen peroxide : propionic acid employed is increased to 1.4 – 1.5.

Thus the examples indicate as an appropriate limit for the ratio of hydrogen peroxide : water at the start of the reaction, 1.2, which of course includes 1.22. As a lower limit that ratio can be 0.1 ; a preferred range is 0.3 to 1.0.

What is claimed is:

1. In the process of producing perpropionic acid by reaction of hydrogen peroxide and propionic acid in an aqueous medium and in the presence of sulfuric acid catalyst for the reaction, the improvement which comprises, for the reduction of explosion hazard in the reaction mixture: employing an initial molar ratio of hydrogen peroxide: propionic acid of 0.8 to less than 1.4:1; a temperature of 20°–60° C; a weight ratio of hydrogen peroxide: water before the start of the reaction thereof with propionic acid, based on 100% hydrogen peroxide, of up to 1.2, the concentration of the sulfuric acid in the reaction mixture being 10–40% by weight.

2. Process of claim 1, wherein the temperature is 30°–45° C.

3. Process of claim 1, wherein the ratio of hydrogen peroxide to water is at least 0.1.

4. Process of claim 1, wherein the ratio of hydrogen peroxide to water is 0.3 to 1.0.

5. Process of claim 1, wherein said reaction gives an equilibrium mixture of perpropionic acid, propionic acid, hydrogen peroxide, water, and acid catalyst.

6. Process of claim 4, wherein said reaction gives an equilibrium mixture of perpropionic acid, propionic acid, hydrogen peroxide, water, and acid catalyst.

* * * * *